US006927212B2

United States Patent
Khan et al.

(10) Patent No.: US 6,927,212 B2
(45) Date of Patent: Aug. 9, 2005

(54) DESIGN AND SYNTHESIS OF RENAL DIPEPTIDASE INHIBITORS

(75) Inventors: Saeed R. Khan, Owings Mills, MD (US); Bert Vogelstein, Baltimore, MD (US); Kenneth W. Kinzler, Bel Air, MD (US); Hallur Gurulingappa, Baltimore, MD (US); Phillip Buckhaults, Columbia, SC (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 10/627,991

(22) Filed: Jul. 28, 2003

(65) Prior Publication Data

US 2004/0091422 A1 May 13, 2004

Related U.S. Application Data

(60) Provisional application No. 60/437,270, filed on Dec. 30, 2002, provisional application No. 60/427,266, filed on Nov. 18, 2002, and provisional application No. 60/398,653, filed on Jul. 27, 2002.

(51) Int. Cl.[7] ............................. A61K 31/66; C07F 9/02
(52) U.S. Cl. ........................................ 514/114; 568/8
(58) Field of Search ................................ 568/8; 514/114

(56) References Cited

PUBLICATIONS

Buckhaults P., et al., "Secreted and cell surface genes expressed in benign and malignant colorectal tumors", *Cancer Research*, (2001) vol. 61, pp. 6996–7001.
Parsons W., et al., "A new class of potent, slowly reversible dehydropeptidase inhibitors", *Biochemical International*, (1991) vol. 23, pp. 1107–1115.
Harper C., et al., "Renal Dipeptidase: Localization and Inhibition", *Biochemica Et Biophysica Acta*, (1971) vol. 242, pp. 446–458.
Accession No: 2003:114414. Tetrahedron Letters, 2003 Gurulingappa, Hallur et al., Design, synthesis and evaluation of new RDP inhibitors listed in Tetrahedron Letters (2003), vol. 44, No. 9, abstract.

*Primary Examiner*—Rita Desai
(74) *Attorney, Agent, or Firm*—Banner & Witcoff, Ltd.

(57) ABSTRACT

Aminophosphinic acid derivatives were synthesized as potential inhibitors of renal dipeptidase, an enzyme overexpressed in benign and malignant colon tumors. Several compounds showed potent enzyme-inhibitory activity. These compounds can be used therapeutically and diagnostically for treatment and detection of tumors.

8 Claims, 5 Drawing Sheets

FIG. 3A
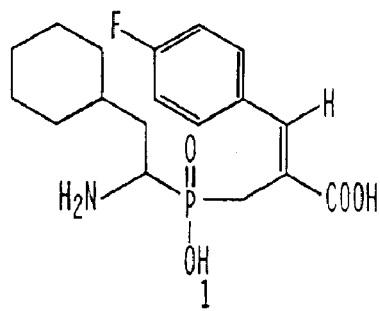
1
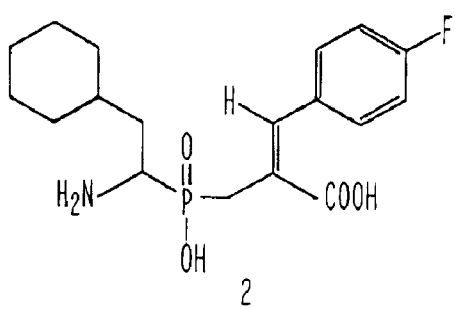
2
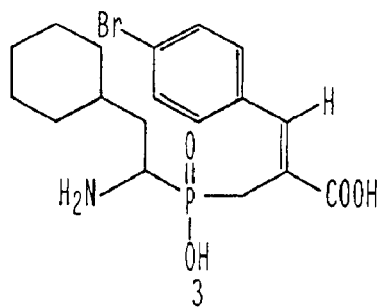
3
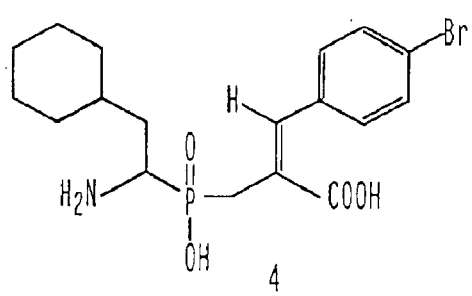
4
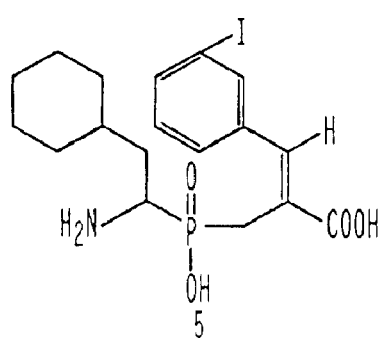
5
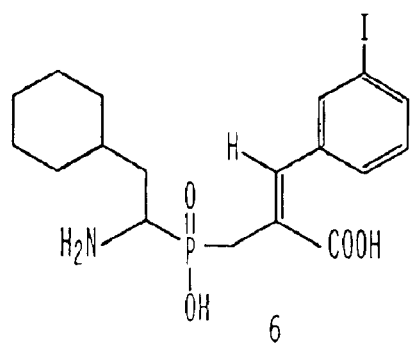
6
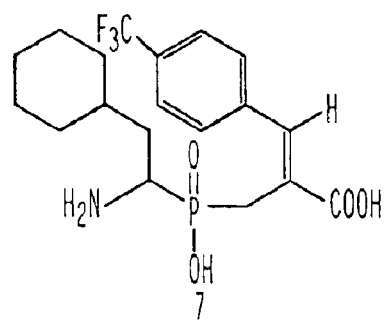
7
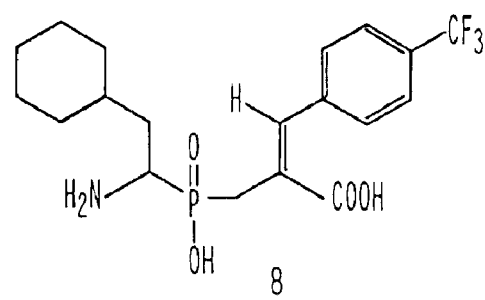
8

FIG. 3B
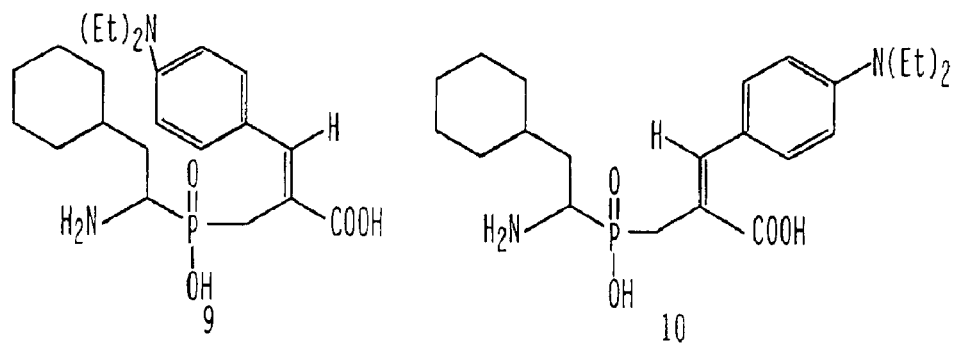
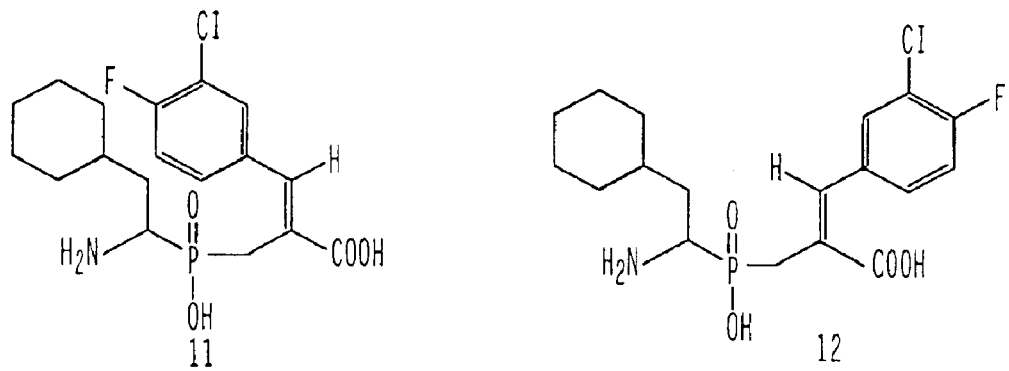
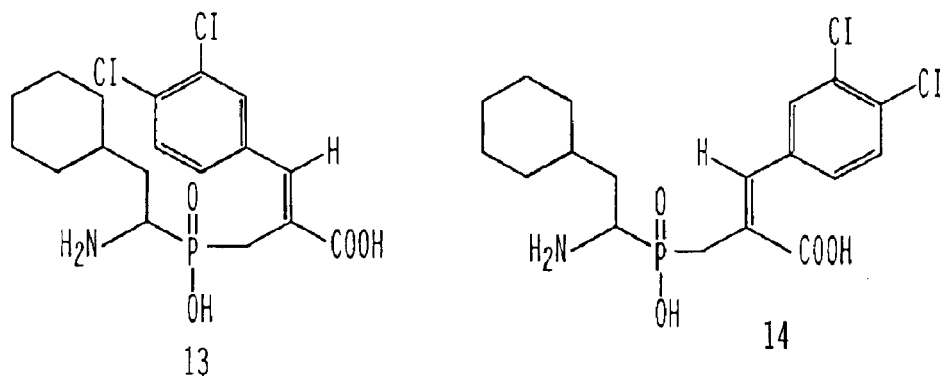
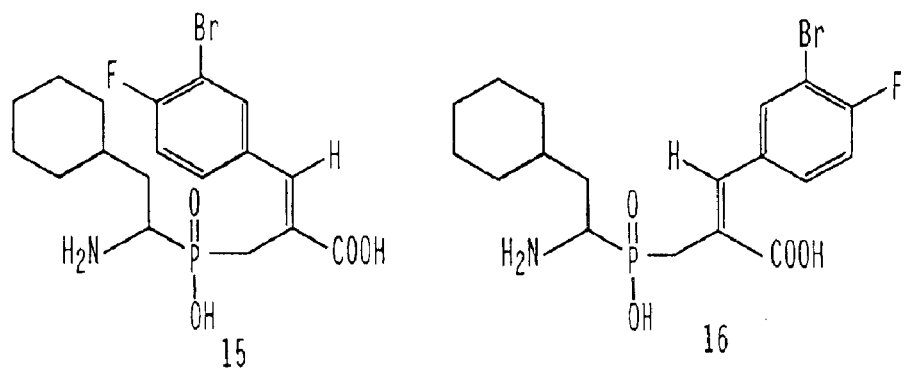

DESIGN AND SYNTHESIS OF RENAL DIPEPTIDASE INHIBITORS

This application claims priority to the three provisional U.S. Applications: Ser. No. 60/427,266 filed Nov. 18, 2002; Ser. No. 60/437,270 filed Dec. 30, 2002; Ser. No. 60/398,653 filed Jul. 27, 2002. The disclosure of each of these applications is expressly incorporated herein.

This invention was made using funds from the United States government, particularly grants from the National Institutes of Health CA 57345 and CA 62924. The U.S. Government therefore retains certain rights in the invention.

FIELD OF THE INVENTION

The invention relates to diagnosis and therapy of tumors. In particular it relates to compounds useful for diagnosis and therapy of tumors.

BACKGROUND OF THE INVENTION

Colon cancer is the second most common cancer in the U.S. and kills more than 50,000 people each year, but it is also one of the most preventable cancers. Screening provides the best prevention. With regular screening, precancerous polyps can be detected and removed, thus preventing the development of colon cancer. Current screening tests such as sigmoidoscopy, colonoscopy and detection of fecal occult blood have significant problems, which have stimulated the search for more specific non-invasive tests for the early detection of colorectal cancers. In recent Serial Analysis of Gene Expression (SAGE) studies performed on normal, adenomatous and cancerous colonic epithelium, the enzyme Renal Dipeptidase (RDP) was found to be overexpressed in both benign and malignant tumor compared with normal colonic epithelium.1

RDP is a glycosylphosphatidyl inositol-anchored enzyme whose major site of expression is the epithelial cells of the proximal tubule of the kidney. The enzyme has been extensively analyzed with respect to its catalytic mechanism and inhibition kinetics by variety of synthetic inhibitors. RDP is unique among the dipeptidases in that it can cleave amine bonds in which the COOH-terminal partner is a D-amino acid, providing an excellent opportunity for the development of specific probes for its detection in vivo.

RDP has been extensively analyzed with respect to its catalytic mechanism and inhibition kinetics by a variety of synthetic inhibitors.2–4 The crystal structure of human renal dipeptidase showed it to be a homodimer with each subunit consisting of a 369 amino acid residue peptide (42 kDa).5 RDP is a zinc-containing hydrolytic enzyme that shows preference for dipeptide substrates with dehydro amino acids at the carboxyl position. Morover, it can accommodate substrates with both D- or L-amino acids at that position, providing an excellent opportunity for the development of specific probes for its detection in vivo.6 α-Aminophosphinic acids, the phosphorous analogues of natural occurring α-aminocarboxylic acids, have received increasing interest in medicine7 and synthetic organic chemistry.8–10 The crystal structure of RDP-cilastatin complex5 has demonstrated that the dipeptidyl moiety of cilastatin is sandwiched between the negatively charged and positively charged sidewalls. Both ends of the moiety are clamped tightly by hydrophobic interactions. Certain aminophosphinic acid derivatives bind to the active site of RDP similar to dipeptides.12

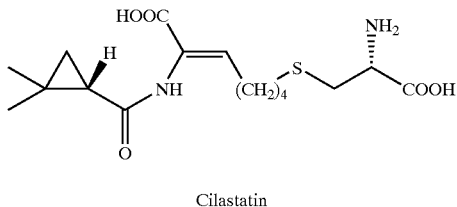

Cilastatin

Dehydropeptide analogs whose scissile carboxamide has been replaced with a $PO(OH)CH_2$ group have been found to be potent inhibitors of the zinc protease dehydrodipeptidase 1 (DHP-1 renal dipeptidase, EC 304.13.11). α-aminophosphinic acids bearing a hydrophobic side chain have been found to inhibit APN in the $10^{-7}$ molar range. Phosphinate analogs have been reported for inhibition of enzymatic activity of VanX.

There is a continuing need in the art for compounds which are useful for diagnosis and therapy of cancers.

BRIEF SUMMARY OF THE INVENTION

In a first embodiment of the invention a compound is provided of formula I:

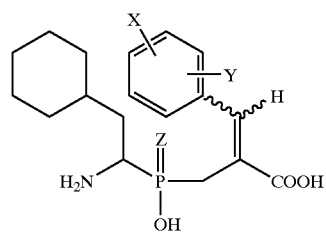

E&Z-isomers wherein

X is selected from the group consisting of F, Cl, Br, $I^{125}$, I, $CF_3$, NR', and radioisotopes thereof;

Y is selected from the group consisting of H, $CH_3$, $OCH_3$, $CF_3$, F, Cl, I, $I^{125}$, NR', and radioisotopes thereof;

NR' is selected from $NH_2$, N(C1 to C6 alkyl)$_2$, and NH(C1 to C6 alkyl);

Z is selected from the group consisting of O, S, and radioisotopes thereof.

In a second embodiment of the invention a diagnostic formulation is provided which comprises a compound of formula I:

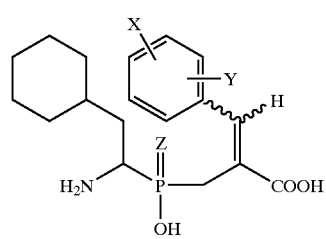

E&Z-isomers wherein

X is selected from the group consisting of F, Cl, Br, $I^{125}$, I, $CF_3$, NR', and radioisotopes thereof;

Y is selected from the group consisting of H, CH$_3$, OCH$_3$, CF$_3$, F, Cl, I, I$^{125}$, NR', and radioisotopes thereof;

NR' is selected from NH$_2$, N(C1 to C6 alkyl)$_2$, and NH(C1 to C6 alkyl);

Z is selected from the group consisting of O, S, and radioisotopes thereof.

In a third embodiment of the invention a method is provided for detecting a tumor. The method comprises:

administering to a subject suspected of carrying a tumor a compound of formula I:

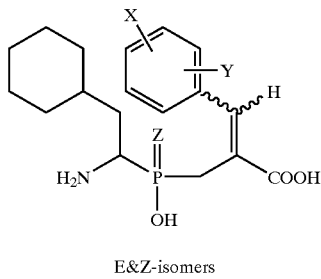

E&Z-isomers wherein

X is selected from the group consisting of F, Cl, Br, I$^{125}$, I, CF$_3$, NR', and radioisotopes thereof;

Y is selected from the group consisting of H, CH$_3$, OCH$_3$, CF$_3$, F, Cl, I, I$^{125}$, NR', and radioisotopes thereof;

NR' is selected from NH$_2$, N(C1 to C6 alkyl)$_2$, and NH(C1 to C6 alkyl);

Z is selected from the group consisting of O, S, and radioisotopes thereof;

detecting localization of the compound within the subject, wherein the localization is not in the proximal tubules of the kidneys; wherein a localization of the compound indicates a tumor at the localization.

In a fourth embodiment of the invention a method is provided method of inhibiting tumor growth. The method comprises:

administering to a subject carrying a tumor a compound of formula I:

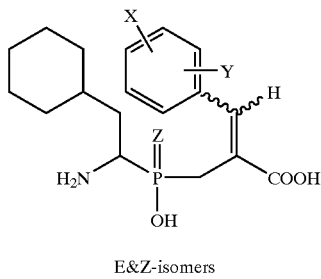

E&Z-isomers wherein

X is selected from the group consisting of F, Cl, Br, I$^{125}$, I, CF$_3$, NR', and radioisotopes thereof;

Y is selected from the group consisting of H, CH$_3$, OCH$_3$, CF$_3$, F, Cl, I, I$^{125}$, NR', and radioisotopes thereof;

NR' is selected from NH$_2$, N(C1 to C6 alkyl)$_2$, and NH(C1 to C6 alkyl);

Z is selected from the group consisting of O, S, and radioisotopes thereof;

whereby growth of the tumor is inhibited.

BRIEF DESCRIPTION OF THE DRAWINGS

FIGS. 3A and 3B show additional inhibitors of RDP numbered 1–16. These are prepared according to Example 4.

Figure 1:
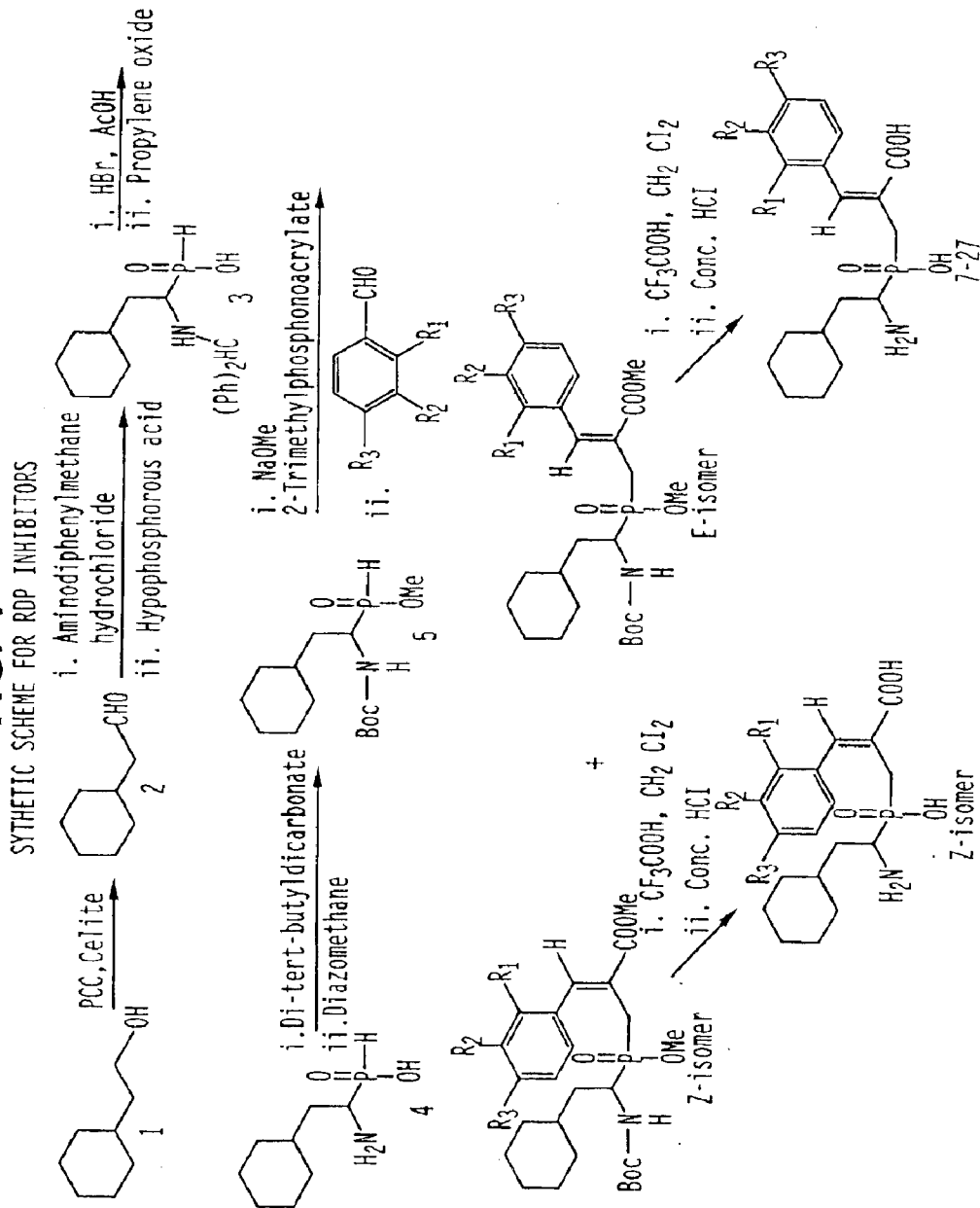
FIG. 1 shows a synthetic scheme for making compounds of formula I.
Figure 2:
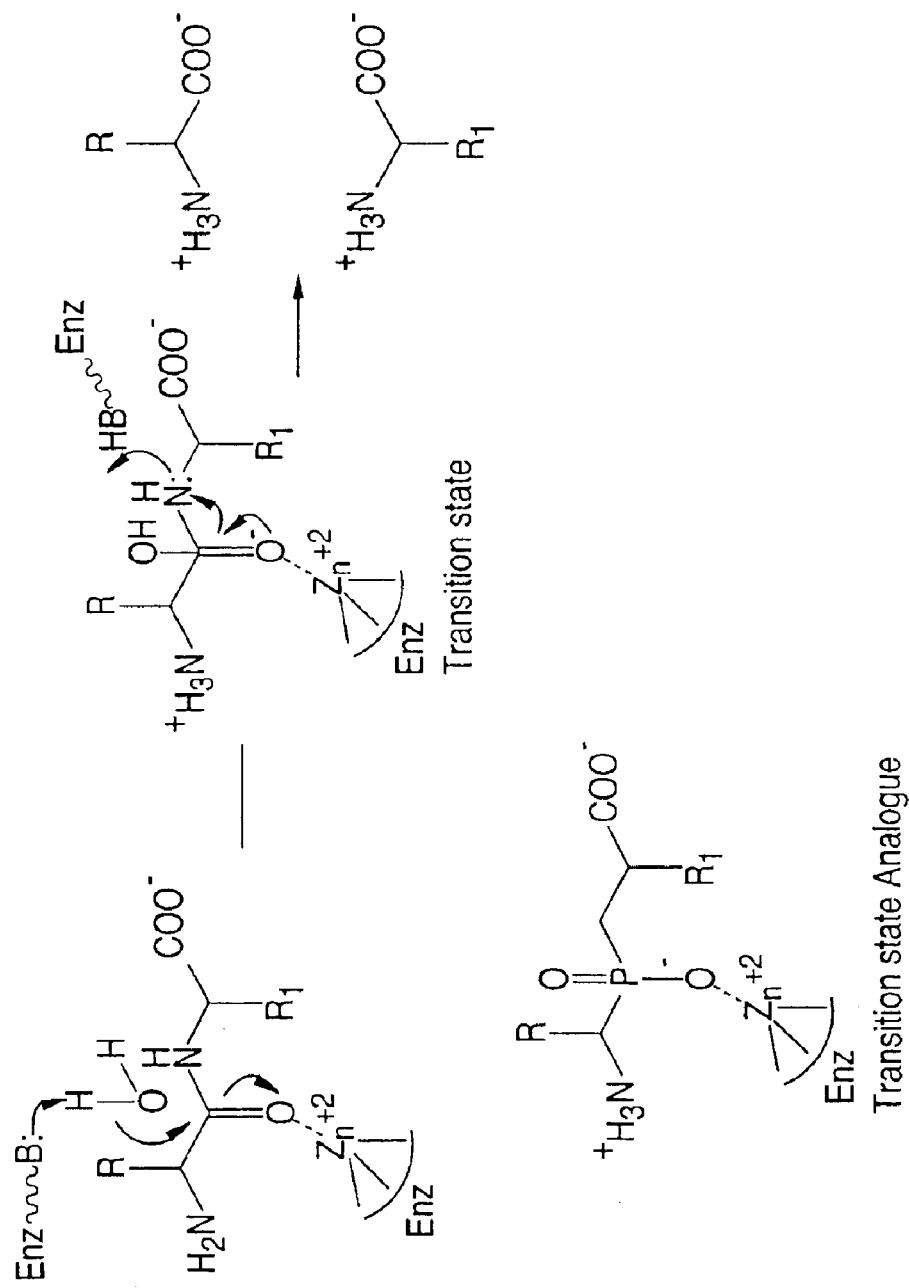
FIG. 2 shows a proposed mechanism of action of renal dipeptidase on a on alkyl amino phosphonic acid derivative. These stable molecules with tetrahedral phosphorus species mimic the tetrahedral intermediate of the reaction catalyzed by RDP. Thus they inhibit the RDP reversibly.
Figure 4:
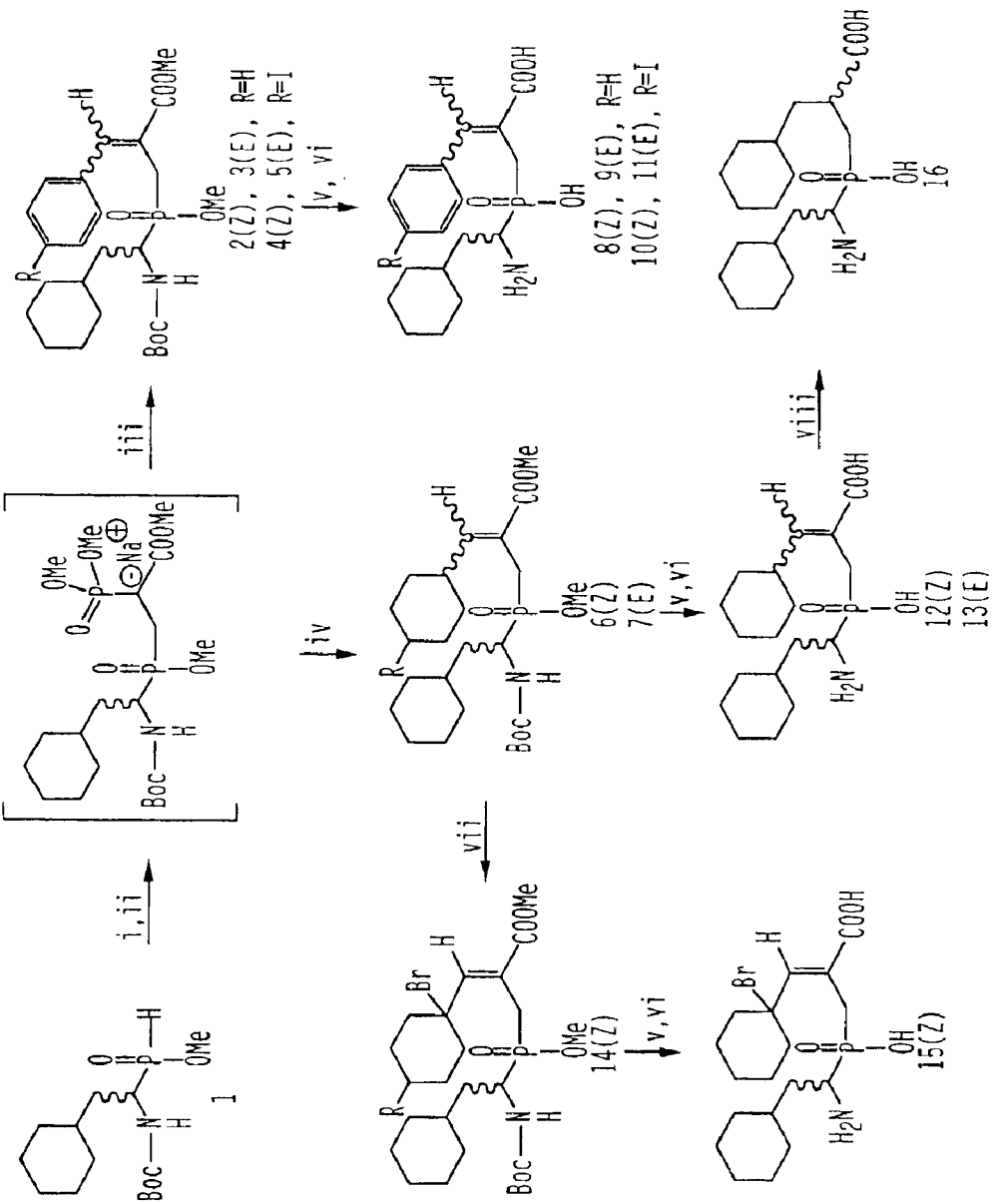
FIG. 4 shows a sheme for making compounds whose activity is shown in Tables 1 and 2.

Tables 1, 2, and 3 show inhibitory characteristics for particular compounds of formula I. $R_1$, $R_2$, and $R_3$ in Table 1 and 2 are substituents on the benzene ring of formula I, also called X and Y. Whereas X and Y have no fixed position on the benzene ring, $R_1$, $R_2$, and $R_3$ have positions as shown in the final formula of FIG. 1. Table 3 refers to the compounds shown in FIG. 4.

DETAILED DESCRIPTION OF THE INVENTION

The invention may be embodied in various forms.

The compound of the invention may be in either the E or the Z isomer. Thus the benzene ring may reside on the same or the opposite side of the double bond from the carboxylic acid group. Either isomer is active in the invention. Any halogen or C1 to C6 haloalkyl or C1 to C6 di- or trihaloalkyl or C1 to C6 alkyl can be used as the group designated as X in formula I. These include radioactive isotopes of the halogens. Similarly, Y can be any halogen or C1 to C6 haloalkyl, or C1 to C6 alkoxy group or C1 to C6 di- or trihaloalkyl or C1 to C6 alkyl. X and Y can also be an amine selected from NH$_2$, N(C1 to C6 alkyl)$_2$, and NH(C1 to C6 alkyl). Again, groups comprising radioactive isotopes of these are included. Z can be either O or S, or a radioisotope thereof.

Formulations of the present invention can be any which are safe and relatively non-toxic to the subject. The formulation can be specifically designed for oral administration to a human subject, for example, comprising agents for flavoring or agents to enhance absorption through the intestines. Alternatively, the compound can be formulated for intravenous administration. Desirably such formulations will be free of pyrogenic substances and sterile to minimize adverse reactions.

Upon administration the compound of the invention will localize to places in the body where the enzyme renal dipeptidase is expressed. The enzyme is typically expressed in the proximal tubules of the kidneys. Localization to this location can be disregarded. However, localization to other locations in the body will indicate a tumor, benign or malignant. The tumor may be in the colon or in any other organ to which colon cancers metastasize. The tumor may also be of other organ origin, such as prostate, breast, stomach, lung, brain, pancreas, or others. Localization to any location other than the proximal tubules of the kidneys can be regarded as a pathological finding.

Detection of the compound of formula I in the body of the subject can be by any means known in the art. If the compound is radioisotopically labeled the compound can be detected by a scanning technique, such as PET scanning, radionuclide scanning, or scintigraphy. Those of skill in the art will recognize how these techniques are performed as well as variations thereof. The choice of particular technique used is well within the skill of the art.

Gamma or positron emitting isotopes are particularly useful for imaging target sites both in vivo and in vitro. Examples of gamma or positron emitting isotopes include Tc-99m, Ga-67, Ga-68 or In-111. For positron emission tomography, Sc-43, Sc-44, Fe-52, Co-55 and Ga-68 may be employed. For fluorescence diagnostic techniques, lanthanides may be employed, in particular Pr, Nd, Sm, Eu, Gd, Tb, Dy, Ho, Er, Tm and Yb. Paramagnetic diagnostic techniques typically employ iron such as Fe-54, Fe-56, Fe-57 and Fe-58. Qualitative and quantative measurements can be made with instrumentation sensitive to each of these forms of emission, or properties (optical or magnetic), available in the art. Other labels can be used as well as radioisotopic labels. Such labels include antigen tags and other fluoresent labels. Again those of skill in the art will readily recognize these techniques and choose them when appropriate.

Because the compounds of the invention have been found to specifically inhibit renal dipeptidase, they can be used therapeutically as well. They can be used to inhibit tumor growth. For such purpose, they may but need not be radioactively labeled. Radioactive labels for such puprose may be different atoms than those for diagnostic puposes. For example, alpha particle, beta particle or Auger electron emitting isotopes may be more desirable than gamma emitters for this purpose, to achieve a cytotoxic effect on tumor cells. Suitable alpha emitters include, bismuth-211, bismuth-212, bismuth-213, and bismuth-214. Useful beta particle emitting isotopes include Sc-46, Sc-47, Sc-48, Ga-72 and Ga-73.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

EXAMPLES

Example 1

Synthesis of Compounds

Compounds were syntheszied using the Witting-Horner reaction. See FIG. 1. These stable tetrahederal phosphorus species act by mimicking the tetrahedral intermediates of the reactions catalyzed by the RDP enzyme.

We report here the synthesis and biological evaluation of new RDP inhibitors. The method employed for the preparation of aminophosphinic acid derivatives is outlined in FIG. 1. Compound 1 was prepared by the condensation of cyclohexylacetaldehyde, hypophosphoric acid and aminodiphenylmethanehydrochloride,[11] followed by protection of the $NH_2$ and P—OH groups with BOC and $CH_2N_2$,[12] respectively. Reaction of 1 with trimethyl-2-phosphonoacrylate in the presence of NaOMe as base gave an intermediate, which subsequently underwent a Wittig-Horner olefination[13] with aldehydes to give mixtures of E and Z isomers, which were separated by column chromatography over silica gel. The yields were 30–40% for the Z isomers and 20–30% for the E isomers. The protecting groups were removed by treatment with $CF_3COOH$ followed by conc. HCl,[12] and the crude products were purified by column chromatography over silica gel to give 8–11. Known compounds 6 and 7 were prepared[12] for comparison. The reaction of 6 with NBS gave a mixture of products from which 14 was isolated in 17% yield. Removal of the protective groups of 14 gave the corresponding free acid 15.15 The dihydro derivative 16 was prepared by catalytic hydrogenation of 12 and 13. All compounds were purified by column chromatography over silica gel and their structures were unambiguously confirmed by spectroscopic methods.[16-17]

Example 2

Assay for Activity of Compounds

The assay buffer was prepared by mixing 20 mM Tris, pH=8, 10 μM ZnCl2; 1 mM substrate (ε-DNP-L-Lys-D-Amp) stock solution in DMSO was prepared. Inhibitors were diluted from MeOH stock solution in water. 20μ of lysate was taken in 150 μl of assay buffer and 20 μl of inhibitor was added. The mixture was incubated at room temperature for 30 min. It was then transferred to plate temperature for 30 min. It was then transferred to plate containing 2 μl/well, 1 mM substrate in DMSO. After mixing incubated at 37° C. Florescence was measured at 30 sec intervals. The IC50 values were determined using small intestine lysate. Ki values were determined for selected compounds using colon cancer lysate.

Example 3

Inhibitory Activity of Compounds

Compounds according to the invention were assayed as described in Example 2. Results of these assays are shown in Tables 1 and 2. Compounds 8, 10, and 12 appear to have the lowest $IC_{50}$.

The RDP inhibition activity of these compounds was determined using crude lysates prepared from human colon cancers. The results are expressed as the concentration of inhibitor needed to inhibit enzyme activity by 50% ($IC_{50}$). The data for the synthesised compounds are shown in Table 1. Human colon cancer extracts were prepared by homogenizing one $cm^3$ of frozen colon tissue in 10 ml of 20 mM Tris, pH 8.0, 10 μM $ZnCl_2$, 0.1% Triton X 100. The extract was clarified by centrifugation at 13,000×g for 5 minutes at 4° C. and, for each measurement, 20 μl was diluted into 158 μl of 20 mM Tris, pH 8.0, 10 μM $ZnCl_2$. 20 μl of the synthesised compounds were added to each reaction to obtain final concentrations ranging from 0 to 10 μM. The mixtures were incubated at room temperature for 30 minutes to allow enzyme-inhibitor complex formation, and the reactions were initiated by the addition of 2 μl of 1 mM substrate (εDNP-L-Lys-D-Amp).[14] While incubating at 37° C., fluorescence (λex=320 nm, λem=405 nm) measurements were determined at 30 sec intervals and the relative reaction rate was taken as the rate of increase of fluorescence over time.

From the data in Table 1, it is apparent that compounds 8, 10 and 12 are potent RDP inhibitors while 15 and 16 are far less active. In general, compounds with the Z configuration (8, 10, and 12) are significantly more active than their E counterparts (9, 11 and 13).

Example 4

General Method of Preparation for Compounds 1–16 as Shown in FIGS. 3A and 3B

A solution of 0.504 g (1.64 mmol) methyl —N-Boc-1-amino-2-cyclohexylethyl phosphinate in 2.5 ml dry methanol at 00 C, was treated drop wise over ten minutes with 0.90 ml of 2.0N methanolic sodium methoxide (1.8 mmol, 1.1 eq). When addition of the base is complete, 0.38 mL (0.48 g, 2.44 mmol, 1.5 eq.) of 2-trimethylphosphono-acrylate was added drop wise over 2 minutes. The mixture is warned to room temperature and stirred for 30 minutes. The mixture was re-cooled to 00 C. and 2.0 eq of substituted benzaldehyde was added drop wise over 2 minutes. The mixture was warmed to room temperature when addition of aldehyde was complete. After 1 hour at room temperature the mixture was diluted with ethyl acetate and washed with phosphate buffer. The organic layer was separated and washed with brine and dried over sodium sulphate. After filtration and removal of volatiles in vacuo, the crude product was purified by medium pressure liquid chromatography. The protecting groups were removed by treatment with trifluoroacetic acid and hydrochloric acid treatment Compound 1. 1H NMR (400 MHz, CD3OD): δ 7.84 (d, 1H, J=4 Hz), 7.68 (d, 2H, J=8 Hz), 7.12 (d, 2H, J=8 Hz), 3.62 (m, 1H), 3.09 (m, 2H), 0.85–1.83 (m, 13 H); LC-MS m/z 369 [M]+.

Compound 2. 1H NMR (400 MHz, CD3OD): δ 7.67 (d, 2H, J=8 Hz), 7.14 (d, 2H, J=8 Hz), 6.95 (d, 1H, J=4 Hz), 3.62 (m, 1H), 3.10 (m, 2H), 0.88–1.81 (m, 13H); LC-MS m/z 369 [M]+.

Compound 3. 1H NMR (400 MHz, CD3OD): δ 7.78 (d, 1H, J=4 Hz), 7.55 (d, 2H, J=8 Hz), 7.47 (d, 2H, J=8 Hz), 3.60 (m, 1H), 3.11 (m, 2H), 0.83–1.85 (m, 13H); LC-MS m/z 430 [M]+.

Compound 4. 1H NMR (400 MHz, CD3OD): δ 7.44 (d, 2H, J=8 Hz), 7.14 (d, 2H, J=8 Hz), 6.95 (d, 1H, J=4 Hz), 3.63 (m, 1H), 3.11 (m, 2H), 0.86–1.82 (m, 13H); LC-MS m/z 430 [M]+.

Compound 5. 1H NMR (400 MHz, CD3OD): δ 8.0 (d, 1H, J=4 Hz), 7.77 (d, 1H, J=4.4 Hz), 7.70 (d, 1H, J=8 Hz), 7.64 (d, 1H, J=8 Hz) 7.17 (t, 1H, J=8 Hz) 3.64 (m, 1H), 3.12 (m, 2H), 0.83–1.84 (m, 13H); LC-MS m/z 369 [M]+.

Compound 6. 1H NMR (400 MHz, CD3OD): δ 7.61 (d, 1H, J=8 Hz), 7.27 (d, 1H, J=4.4 Hz), 7.23 (d, 1H, J=8 Hz), 7.07 (t, 1H, J=8 Hz) 6.92 (d, 1H, J=4 Hz) 3.62 (m, 1H), 3.14 (m, 2H), 0.85–1.87 (m, 13H); LC-MS m/z 369 [M]+.

Compound 7. 1H NMR (400 MHz, CD3OD): δ 7.88 (d, 1H, J=4 Hz), 7.78 (d, 2H, J=8 Hz), 7.68 (d, 2H, J=8 Hz), 3.64 (m, 1H), 3.12 (m, 2H), 0.82–1.84 (m, 13H); LC-MS m/z 419 [M]+.

Compound 8. 1H NMR (400 MHz, CD3OD): δ 7.58 (d, 2H, J=8 Hz), 7.37 (d, 2H, J=8 Hz), 7.05 (d, 1H, J=4 Hz), 3.63 (m, 1H), 3.14 (m, 2H), 0.85–1.83 (m, 13H); LC-MS m/z 419 [M]+.

Compound 9. 1H NMR (400 MHz, CD3OD): δ 7.77 (d, 1H, J=4 Hz), 7.57 (d, 2H, J=8 Hz), 6.68 (d, 2H, J=8 Hz), 3.64 (m, 1H), 3.11 (m, 2H), 0.84–1.82 (m, 13H) LC-MS m/z 422 [M]+.

Compound 10. 1H NMR (400 MHz, CD3OD): δ 7.64 (d, 2H, J=8 Hz), 6.67 (d, 2H, J=8 Hz), 6.56 (d, 1H, J=4 Hz), 3.63 (m, 1H), 3.13 (m, 2H), 0.87–1.83 (m, 13H); LC-MS m/z 422 [M]+.

Compound 11. 1H NMR (400 MHz, CD3OD): δ 7.79 (d, 1H, J=4 Hz), 7.78 (m, 1H), 7.61 (m, 1H), 7.20 (m, 1H), 3.64 (m, 1H), 3.10 (m, 2H), 0.87–1.84 (m, 13H); LC-MS m/z 403 [M]+.

Compound 12. 1H NMR (400 MHz, CD3OD): δ 7.78 (m, 1H), 7.61 (m, 1H), 7.20 (m, 1H), 6.92 (d, 1H, J=4 Hz), 3.66 (m, 1H), 3.11 (m, 2H), 0.85–1.83 (m, 13H); LC-MS m/z 403 [M]+.

Compound 13. 1H NMR (400 MHz, CD3OD): δ 7.82 (d, 1H, J=4 Hz), 7.77 (m, 1H), 7.55 (m, 1H), 7.50 (m, 1H), 3.63 (m, 1H), 3.11 (m, 2H), 0.86–1.82 (m, 13H); LC-MS m/z 420 [M]+.

Compound 14. 1H NMR (400 MHz, CD3OD): δ 7.75 (m, 1H), 7.39 (m, 1H), 7.12 (m, 1H), 6.91 (d, 1H, J=4 Hz), 3.65 (m, 1H), 3.13 (m, 2H), 0.84–1.86 (m, 13H); LC-MS m/z 420 [M]+.

Compound 15. 1H NMR (400 MHz, CD3OD): δ 7.85 (d, 1H, J=4 Hz), 7.77 (m, 1H), 7.57 (m, 1H), 7.17 (m, 1H), 3.63 (m, 1H), 3.11 (m, 2H), 0.85–1.87 (m, 13H); LC-MS m/z 448 [M]+.

Compound 16. 1H NMR (400 MHz, CD3OD): δ 7.49 (m, 1H), 7.20 (m, 1H), 7.07 (m, 1H), 6.91 (d, 1H, J=4 Hz), 3.64 (m, 1H), 3.10 (m, 2H), 0.86–1.84 (m, 13H); LC-MS m/z 448 [M]+.

References

1. Buckhaults, P; Rago, C; Croix, B. S.; Romans, K. E.; Saha, S; Zhang, L; Vogelstein, B.; Kinzler, K. W. *Cancer Res.* 2001, 61, 6996–7001.
2. Kropp, H; Sundelof, J. G.; Hajdu, R.; Kahan, F. M. *Antimicrob. Agents Chemother.* 1982, 22, 62–70.
3. Kahan, F. M.; Kropp, H.; Sundelof, J. G.; Birnbaum, J. *J. Antimicrob. Chemother.* 1983, 12, 1–35.
4. Campbell, B. J.; Shih, Y. D.; Forrester, L. J.; Zahler, W. L. *Biochem. Biophys. Acta* 1988, 956, 110–118.
5. Nitanai, Y.; Satow, Y.; Adachi, H.; Tsujimoto, M. *J. Mol. Biol.* 2002, 321, 177–184.
6. Greenstein, J. P. *Adv. Enzymol. Relat. Subj. Biochem.* 1948, 8, 117–169.
7. Atherton, F. R.; Hassall, C. H.; Lambert, R. W. *J. Med. Chem.* 1986, 29, 29–40.
8. Smith, A. B.; Yager, K. M.; Taylor, C. M. *J. Am. Chem. Soc.* 1995, 117, 10879–10888.
9. Xiao, J.; Zhang, X; Yuan, C. *Heteroatom Chemistry* 2000, 11, 536–540.
10. Wu, Y. Q.; Mobashery, S. *J. Med. Chem.* 1991, 34, 1914–1916.
11. Baylis, E. K.; Campbell, C. D.; Dingwall J. D. *J. Chem. Soc. Perkin Trans.* 1 1984, 2845–2853.
12. Parsons, W. H.; Hajdu, R.; Schoen, W. R.; Combs, P. L.; Sundelof, J.; Patchett, A. A. *Biochem. Intnl.* 1991, 23, 1107–1115.
13. Schoen, W. R.; Parsons, W. H. *Tetrahedron Lett.* 1988, 29, 5201–5204.
14. Ian, J. W.; Jill, L.; Carvell, H. W.; Nigel, M. H. *Anal. Biochem.* 1999, 268, 245–251.
15. Compound 11: $^1$H NMR (400 MHz, CD3OD): δ 7.02 (m, 1H), 3.44 (m, 1H), 3.21 (m, 2H), 0.80–1.85 (m, 23H); $^{13}$C NMR (125 MHz, CD3OD): δ 168.3, 145.0, 125.6, 43.5, 39.5, 38.5, 35.3, 32.8, 31.6, 30.5, 29.2, 28.2, 26.5, 25.2, 24.5, 22.5, 21.6, 19.5; LC-MS m/z 436 [M]$^+$, 438 [M+2]$^+$.
16. Compound 4: $^1$H NMR (400 MHz, CD3OD): δ 7.83 (d, 1H, J=4 Hz), 7.78 (d, 2H, J=8 Hz), 7.46 (d, 2H, J=8 Hz), 3.63 (m, 1H), 3.07 (m, 2H), 0.84–1.82 (m, 13H); $^{13}$C NMR (125 MHz, CD3OD): δ 168.6, 138.5, 137.4, 136.8, 134.2, 128.3, 127.5, 126.2, 95.8, 46.3, 32.4, 31.8, 30.6, 29.2, 28.4, 25.3, 24.5, 19.6; LC-MS m/z 477 [M]$^+$.
17. Compound 5: $^1$H NMR (400 MHz, CD3OD): δ 7.67 (d, 2H, J=8 Hz), 7.14 (d, J=8 Hz), 6.95 (d, 1H, J=4 Hz), 3.62 (m, 1H), 3.10 (m, 2H), 0.88–1.81 (m, 13H); $^{13}$C NMR (125 MHz, CD3OD): δ 169.2, 137.5, 137.2, 136.6, 135.2, 127.5, 126.5, 125.8, 95.3, 46.5, 32.4, 30.8, 31.2, 29.3, 28.2, 25.4, 24.8, 23.6; LC-MS m/z 477 [M]$^+$.

TABLE 1

RDP inhibition (IC$_{50}$ and Ki)$^{a,b}$ values of compounds

| Comp. | R1 | R2 | R3 | Olefin geometry | IC$_{50}$ (nM) | Ki (nM) |
|---|---|---|---|---|---|---|
| 6 | H | H | H | Z | 28 | 1.12 |
| 7 | H | H | H | E | 40 | 1.6 |
| 8 | H | H | F | Z | 5 | 0.6 |
| 9 | H | H | F | E | 15 | 0.72 |
| 10 | H | H | Br | Z | 6 | 0.72 |
| 11 | H | H | Br | E | 30 | 2.4 |
| 12 | H | H | I | Z | 8 | 0.6 |
| 13 | H | H | I | E | 25 | 2.0 |
| 14 | H | I | H | Z | 45 | 3 |
| 15 | H | I | H | E | 250 | 10 |

$^a$IC$_{50}$ Values are determined using small intestine lysate
$^b$Ki Values are determined using colon cancer lysate

TABLE 2

RDP inhibition (IC$_{50}$)$^a$ values of compounds

| Comp. | R1 | R2 | R3 | Olefin geometry | IC$_{50}$ (nM) |
|---|---|---|---|---|---|
| 16 | I | H | H | Z | 100 |
| 17 | I | H | H | E | 2000 |
| 18 | H | H | CF$_3$ | Z | 10 |
| 19 | H | H | CF$_3$ | E | 200 |
| 20 | H | Cl | Cl | Z | 20 |
| 21 | H | Cl | Cl | E | 200 |
| 22 | H | Cl | F | Z | 30 |
| 23 | H | Cl | F | E | 350 |
| 24 | H | Br | F | Z | 40 |
| 25 | H | Br | F | E | 300 |
| 26 | H | H | N(Et)$_2$ | Z | 70 |
| 27 | H | H | N(Et)$_2$ | E | 150 |

$^a$IC$_{50}$ Values are determined using small intestine lysate

TABLE 3

RDP inhibition activity$^a$ of compounds

| Compound | Olefin geometry | IC$_{50}$ (nM) |
|---|---|---|
| 8 | Z | 5.5 |
| 9 | E | 300 |
| 10 | Z | 8 |
| 11 | E | 25 |
| 12 | Z | 3.5 |
| 13 | E | 60 |
| 15 | Z | 45 |
| 16 | E | 300 |

$^a$IC$_{50}$ values were determined using colon cancer lysate.

We claim:

1. A compound of formula I:

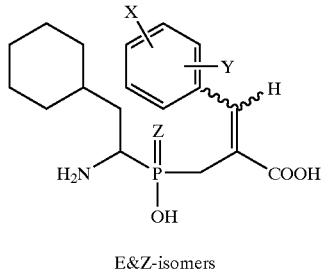

E&Z-isomers wherein

X is selected from the group consisting of F, Cl, Br, $^{125}$I, I, CF$_3$, NR', and radioisotopes thereof;

Y is selected from the group consisting of H, CH$_3$, OCH$_3$, CF$_3$, F, Cl, $^{125}$I, NR', and radioisotopes thereof;

NR' is selected from NH$_2$, N(C1 to C6 alkyl)$_2$, and NH (C1 to C6 alkyl);

Z is selected from the group consisting of O, S, and radioisotopes thereof.

2. The compound of claim 1 which is the E isoform.

3. The compound of claim 1 which is the Z isoform.

4. The compound of claim 1 which is radiolabeled.

5. The compound of claim 1 wherein at least one atom of X or Y is radiolabeled.

6. The compound of claim 1 wherein at least one of X or Y is an $^{125}$I atom.

7. A sterile, apyrogenic formulation for intravenous administration to a human subject comprising:

the compound of claim 1; and water.

8. The method of inhibiting colon tumor growth, comprising:

administering to a subject carrying a colon tumor an effective amount of a compound of claim 1, whereby growth of the colon tumor is inhibited.

* * * * *